United States Patent
Denyer et al.

(10) Patent No.: US 9,302,060 B2
(45) Date of Patent: Apr. 5, 2016

(54) APPARATUS AND METHOD COMPRISING ADJUSTABLE STEPPED MOUTHPIECE FOR AEROSOL DRUG DELIVERY

(75) Inventors: Jonathan Stanley Harold Denyer, Chichester (GB); Kurt Verner Holger Nikander, Salem, MA (US); Dirk Ernest Von Hollen, Clark, NJ (US); Gerald Christopher Smaldone, Setauket, NY (US); Ian Thomas Petherbridge, Bognor Regis (GB)

(73) Assignee: KONINKLIJKE PHILIPS N.V., Eindhoven (NL)

(*) Notice: Subject to any disclaimer, the term of this patent is extended or adjusted under 35 U.S.C. 154(b) by 626 days.

(21) Appl. No.: 13/511,828

(22) PCT Filed: Nov. 9, 2010

(86) PCT No.: PCT/IB2010/055092
§ 371 (c)(1),
(2), (4) Date: May 24, 2012

(87) PCT Pub. No.: WO2011/067692
PCT Pub. Date: Jun. 9, 2011

(65) Prior Publication Data
US 2012/0240922 A1 Sep. 27, 2012

Related U.S. Application Data

(60) Provisional application No. 61/266,741, filed on Dec. 4, 2009.

(51) Int. Cl.
*A61M 15/00* (2006.01)
*A61B 13/00* (2006.01)
*A61M 16/04* (2006.01)

(52) U.S. Cl.
CPC ............ *A61M 15/00* (2013.01); *A61M 15/0021* (2014.02); *A61M 16/0493* (2014.02); *A61M 16/0495* (2014.02); *A61M 15/009* (2013.01)

(58) Field of Classification Search
CPC ...................... A61M 16/0021–16/0026; A61M 16/0488–16/0497; A61M 2210/0625–2210/0656; A61M 15/00; A61M 15/0021–15/0026

USPC ............. 128/200.14–15, 200.24, 200.26, 128/202.17, 203.15, 203.23, 206.29, 128/207.14, 210.26, 848, 857, 859–861, 128/862; 433/140
See application file for complete search history.

(56) References Cited

U.S. PATENT DOCUMENTS 3,998,226 A * 12/1976 Harris .................. A61M 15/00
128/203.15
4,148,308 A 4/1979 Sayer
(Continued)

FOREIGN PATENT DOCUMENTS

JP 10512478 A 12/1998
JP 2007520279 A 7/2007
(Continued)

OTHER PUBLICATIONS

Svartengren et al, "Oropharyngeal Deposition of 3.5 μm Particles Inhaled Through an Elongated Mouthpiece", Eur Respir J., vol. 9, 1996, p. 1556-1559.

*Primary Examiner* — Tan-Uyen (Jackie) T Ho
*Assistant Examiner* — Joseph D Boecker
(74) *Attorney, Agent, or Firm* — Michael W. Haas

(57) ABSTRACT

An apparatus (10) and method to aid in administering inhaled pharmaceutical aerosol to a patient is configured to maintain a tongue in proper position and offset the patients upper and lower jaws during aerosol delivery. An adjustable member (26) is provided adjacent a mouthpiece and at least partially surrounds and moves with respect to the body of the apparatus. The adjustable member has a step structured (32, 34) to impart a selected amount of mandibular advancement to a patient during aerosol delivery. A tongue depressor (40) which may be integrally formed with the adjustable member configured to prevent a tongue from occluding a flow of aerosol is also provided.

36 Claims, 7 Drawing Sheets

(56) References Cited

U.S. PATENT DOCUMENTS

| | | | | |
|---|---|---|---|---|
| 4,852,561 | A * | 8/1989 | Sperry | A61M 15/0086 128/200.18 |
| 5,069,619 | A * | 12/1991 | Frisbie | A61C 9/0006 433/214 |
| 5,533,523 | A | 7/1996 | Bass, Jr. et al. | |
| 5,692,493 | A | 12/1997 | Weinstein et al. | |
| 5,752,510 | A * | 5/1998 | Goldstein | A61M 16/0488 128/200.24 |
| 5,941,247 | A * | 8/1999 | Keane | A61F 5/566 128/848 |
| 6,606,992 | B1 | 8/2003 | Smith et al. | |
| 6,964,761 | B1 | 11/2005 | Condos et al. | |
| 6,966,319 | B2 * | 11/2005 | Fitton | A61M 16/0488 128/848 |
| 7,140,365 | B2 | 11/2006 | Poole et al. | |
| 7,464,706 | B2 | 12/2008 | Steiner et al. | |
| 7,984,714 | B2 * | 7/2011 | Hausmann | A61F 5/56 128/848 |
| 8,226,407 | B2 * | 7/2012 | Hanewinkel | A61B 1/24 433/140 |
| 8,783,260 | B2 * | 7/2014 | Remmers | A61F 5/566 128/848 |
| 2003/0010336 | A1 * | 1/2003 | Vito | A61M 15/0086 128/200.22 |
| 2003/0089371 | A1 * | 5/2003 | Robertson | A61M 16/0488 128/201.26 |
| 2004/0177853 | A1 * | 9/2004 | Kownacki | A61F 5/566 128/848 |
| 2005/0217678 | A1 * | 10/2005 | McCormick | A61M 16/0488 128/206.29 |
| 2007/0065367 | A1 | 3/2007 | Condos et al. | |
| 2007/0068534 | A1 * | 3/2007 | Bailey | A61F 5/566 128/848 |
| 2007/0221211 | A1 * | 9/2007 | Sagalovich | A61M 15/0086 128/200.15 |
| 2007/0287598 | A1 * | 12/2007 | Christensen, III | A61B 1/24 482/11 |
| 2008/0292559 | A1 | 11/2008 | Condos et al. | |
| 2011/0104631 | A1 * | 5/2011 | Levine | A61C 19/063 433/29 |
| 2011/0217674 | A1 * | 9/2011 | Hanewinkel | A61B 1/24 433/140 |
| 2011/0240015 | A1 | 10/2011 | Nikander et al. | |
| 2012/0247485 | A1 * | 10/2012 | Timmons | A61F 5/566 128/848 |
| 2013/0089836 | A1 * | 4/2013 | Stapelbroek | A46B 9/045 433/216 |
| 2014/0227657 | A1 * | 8/2014 | Sanders | A61C 19/066 433/32 |
| 2014/0352087 | A1 * | 12/2014 | De Vries | A61C 17/228 15/21.1 |
| 2015/0314163 | A1 * | 11/2015 | Yoshitake | A63B 23/032 601/38 |

FOREIGN PATENT DOCUMENTS

| | | |
|---|---|---|
| WO | 9622802 A1 | 8/1996 |
| WO | 2004064704 A2 | 8/2004 |
| WO | 2005074480 A2 | 8/2005 |
| WO | 2010073148 A1 | 7/2010 |

* cited by examiner

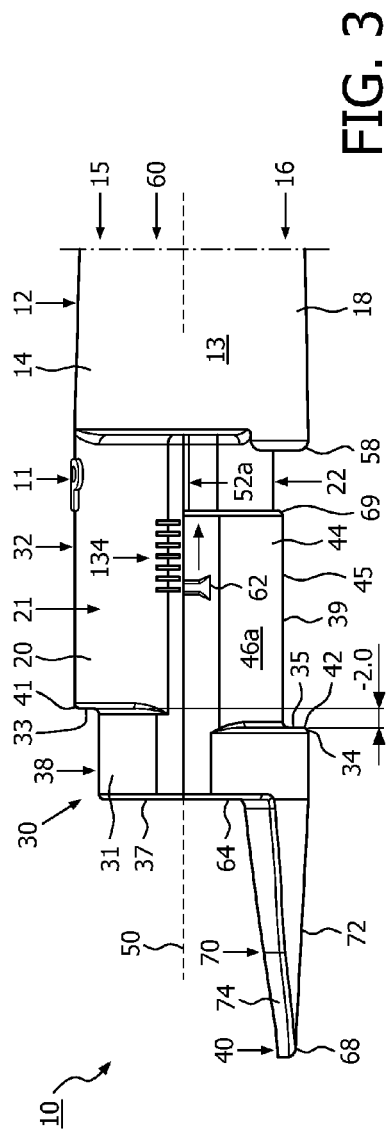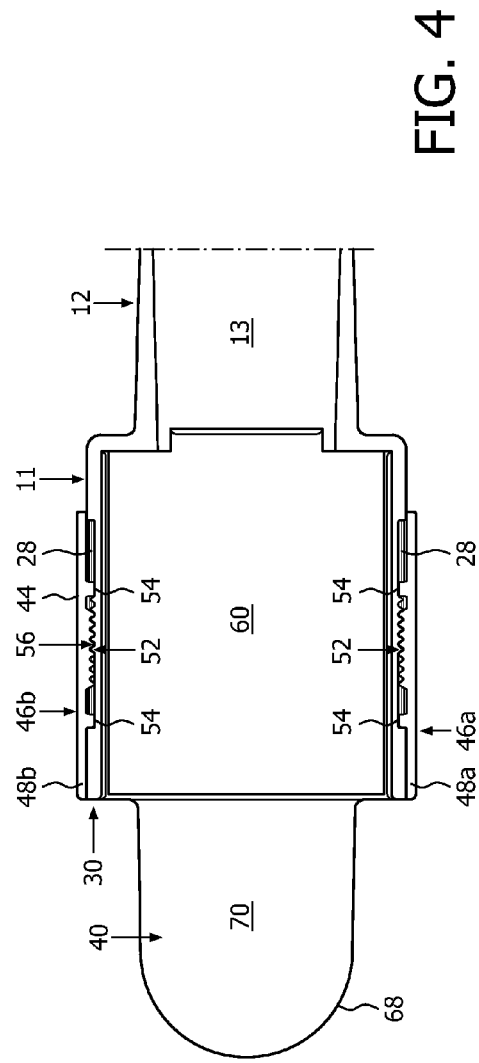

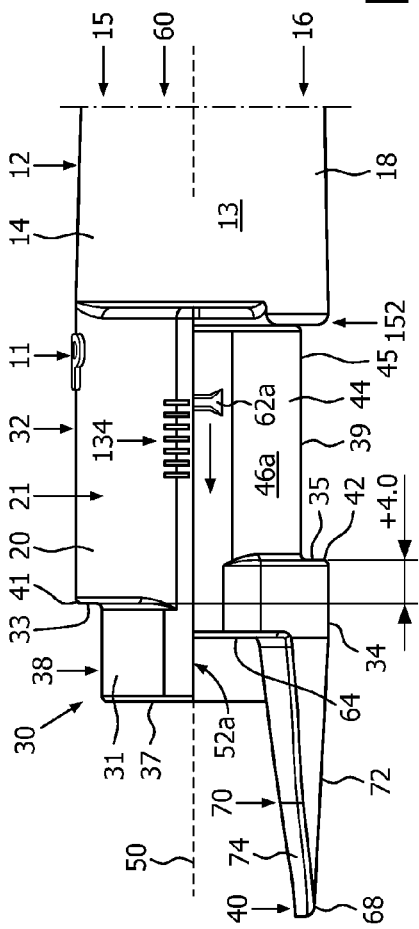
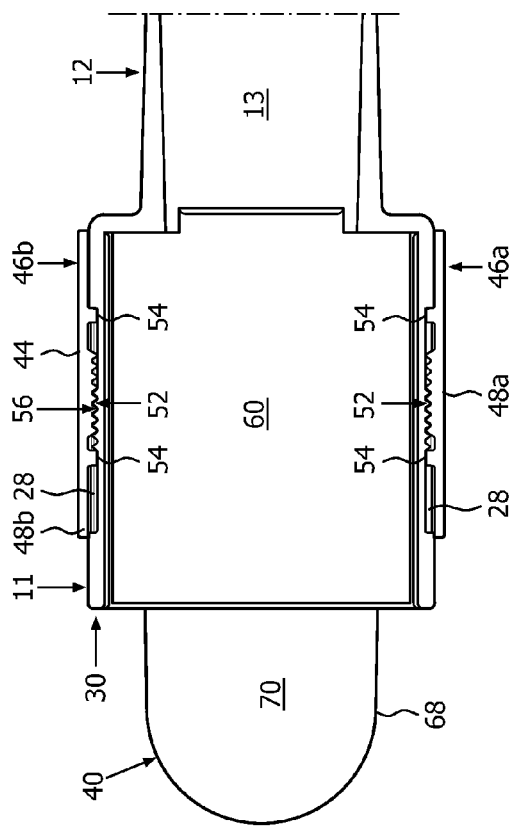

APPARATUS AND METHOD COMPRISING ADJUSTABLE STEPPED MOUTHPIECE FOR AEROSOL DRUG DELIVERY

The present invention is generally related to an apparatus and method to aid in administering inhaled pharmaceutical aerosol to a patient.

Medical devices used to deliver drugs in an aerosol form to patients have been used since the mid 1950s. Such devices are used to deliver inhaled pharmaceutical aerosols (IPAs) into lungs of patients. The most common use of such devices is in the treatment of asthma and chronic obstructive pulmonary diseases, in forms of meter dose inhalers, dry powder inhalers, or nebulizers.

A problem with the use of inhalers is the low efficiency of the delivery of the aerosol to its target. In cases of patient administered meter dose inhalers (MDI) or dry powder inhalers (DPI), for example, up to 50% of the aerosolized drug may not reach the lungs of the patient. Various different ways of trying to improve lung deposition have been attempted, including, but not limited to, teaching patients about optimal positioning of the inhaler mouthpieces, ensuring the patient lips make an effective seal around the mouthpiece of the inhaler, and ensuring that the patient places their teeth around the mouthpiece effectively so as not to obstruct the flow of aerosol.

Although some devices are configured to prevent narrowing of the airway behind the tongue, it may still possible for the patient to obstruct the mouthpiece. Other devices attempt to offset the subject's upper and lower jaws during aerosol delivery, but different patients may have different offset requirements.

One aspect of the present disclosure includes a mouthpiece for an apparatus to aid aerosol delivery to a patient. The mouthpiece includes: a body; a bore extending through the body; an upper step on a top side of the mouthpiece; a lower step on a bottom side of the mouthpiece; and a tongue depressor extending from the bottom side and configured to prevent a tongue from occluding a flow of aerosol through the mouthpiece.

Another aspect of the disclosure includes a mouthpiece for an apparatus to aid aerosol delivery to a patient. The mouthpiece includes: a body; a bore extending through the body; an adjustable member configured to move in a longitudinal direction with respect to the body; an upper step on a top side of the mouthpiece; and a lower step on a bottom side of the mouthpiece. The upper step is formed on one of the body or adjustable member and the lower step is formed on the other of the body or adjustable member. Movement of the adjustable member adjusts a longitudinal distance between the upper step and the lower step.

Yet another aspect of the disclosure includes a mouthpiece for an apparatus to aid aerosol delivery to a patient. The mouthpiece includes: a body; a bore extending through the body; a first step on a top side of the mouthpiece; a second step on a bottom side of the mouthpiece; an adjustable member configured to move in a longitudinal direction with respect to the body, the first step formed on one of the body or adjustable member and the second step formed on the other of the body or adjustable member; and a tongue depressor extending from the second side and configured to prevent a tongue from occluding a flow of aerosol through the mouthpiece.

Another aspect of the disclosure includes an apparatus to deliver pharmaceutical aerosol to a patient including: a pharmaceutical containing reservoir; a mouthpiece operatively connected with the reservoir, the mouthpiece comprising a body; the mouthpiece further comprising a bore extending through the body; an adjustable member configured to move in a longitudinal direction with respect to the body; a first step on a top side of the mouthpiece; and a second step on a bottom side of the mouthpiece. The first step is formed on one of the body or the adjustable member and the second step is formed on the other of the body or the adjustable member.

Yet another aspect of the disclosure includes method for selecting a fixed mouthpiece for an apparatus configured to deliver aerosol to a user using an adjustable mouthpiece, the adjustable mouthpiece including a body; a bore extending through the body; a first step on a top side of the mouthpiece; a second step on a bottom side of the mouthpiece; an adjustable member configured to move in a longitudinal direction with respect to the body so as to adjust a longitudinal distance between the first step and the second step to determine an appropriate offset between the first step and the second step for the user. The method includes: inserting the adjustable mouthpiece into a mouth of a patient; sliding the adjustable member in a longitudinal direction along the body to determine an appropriate offset amount for the user; and selecting a fixed mouthpiece for the apparatus based on the determined offset amount. The offset imparts a selected amount of mandibular shift to the user.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

FIG. 3 is a side view of the apparatus of FIG. 1 in a first position in accordance with an embodiment.

FIG. 4 is a top view of a cross section of the apparatus in the first position shown in FIG. 3.

FIG. 5 is a side view of the apparatus of FIG. 1 in a second position in accordance with an embodiment.

FIG. 6 is a top view of a cross section of the apparatus in the second position shown in FIG. 5.

In one embodiment, an apparatus of the present invention comprises a mouthpiece of such configuration, that when a patient uses the apparatus properly, the mouthpiece will force the patient's lower jaw into a position to increase the deposition of inhaled pharmaceutical aerosol into the patient's lung while depressing the patient's tongue such that it does not occlude the flow of aerosol through the mouthpiece. The apparatus increases the deposition of the inhaled pharmaceutical aerosol in the patient's lungs by improving the geometry of the oral cavity of the patient to cause a laminar flow of an air/inhaled pharmaceutical aerosol mixture. Furthermore, a mouthpiece with an adjustable configuration for offsetting the jaws allows for adjustment of the airway behind the tongue to suit each patient. Positioning each patient's jaw and related anatomical structure in an appropriate way will decrease the deposition of inhaled pharmaceutical aerosol particle in the upper airway, and increase the deposition in the lungs.

Figure 1:
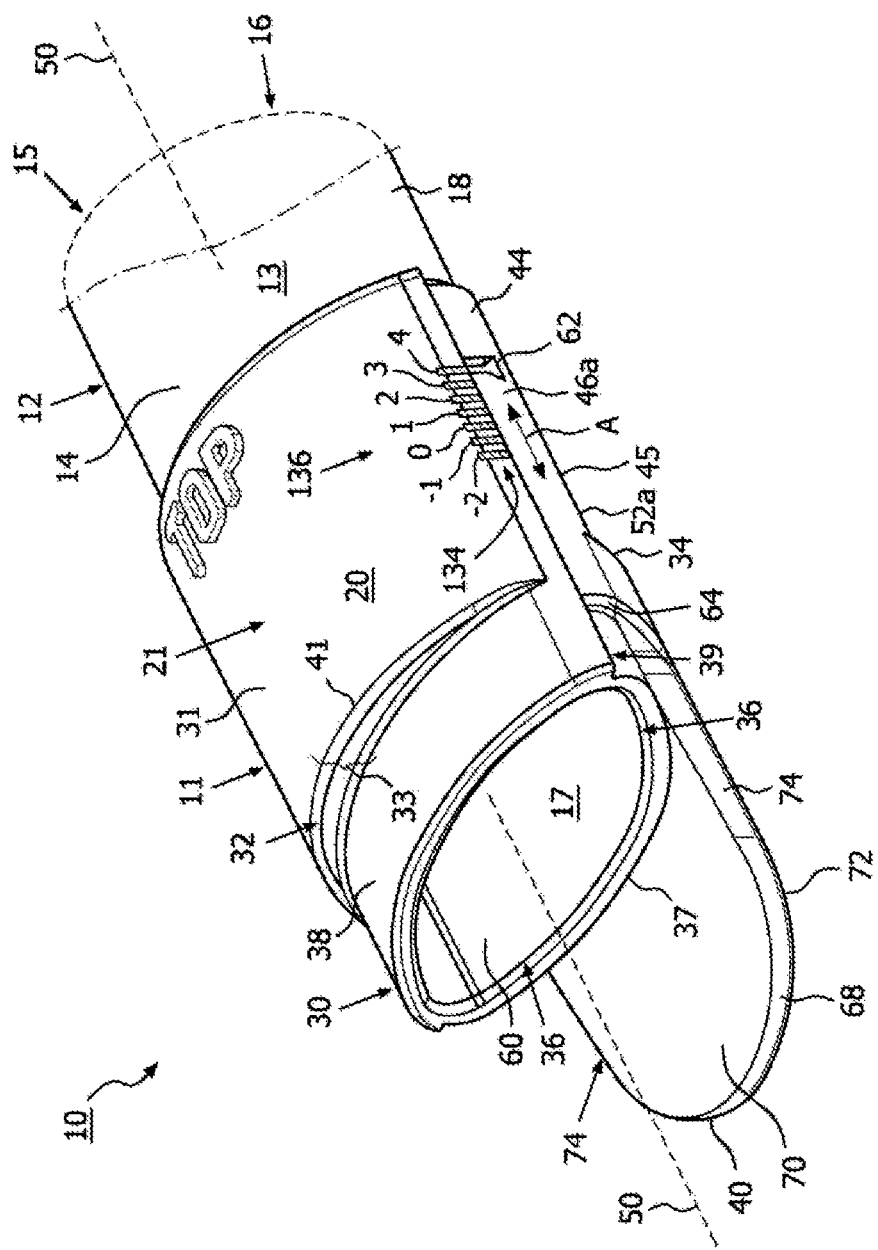
FIG. 1 is a perspective view of an embodiment of an apparatus of the present invention.

Referring now more particularly to the drawings, FIG. 1 illustrates an exemplary embodiment of an apparatus 10 according to one embodiment of the present invention. Apparatus 10 comprises a hollow body 11 with a front end 12, center section 20, and back end 30 with an imaginary axis 50 leading through hollow body 11. Apparatus 10 may be a stand-alone mouthpiece 31 that can be connected to an aerosol generating device (e.g., inhaler or nebulizer) or can be an entire aerosol generator (e.g., inhaler or nebulizer) for which the mouthpiece 31 forms a component, as will be described later. The mouthpiece has an inlet port 13 at front end 12. Apparatus 10 also comprises a bore 60 through the apparatus from front end 12 to the back end 30. Bore 60 terminates on front end 12 with inlet aperture 16, and on back end 30 with outlet aperture 36. Further, apparatus 10 comprises a tongue depressor 40 provided on the bottom of the mouthpiece 31, adjacent back end 30.

The tubular body 11 may be formed from a suitable material. Suitable materials may be any biocompatible material, which is acceptable for a safe and effective use by a patient or a medical professional. Any commonly used material in the art of inhaled pharmaceutical aerosols delivery may be used. The material should also provide a structure to the mouthpiece so that a patient does not deform the mouthpiece during the use thereof. A suitable material may be a thermoset plastic, such as acrylonitrile butadiene styrene, poly(methyl methacrylate), polyacrylate, polyethylene, polypropylene, polybutylene, polysulfone, polyphthalamide, polystyrene, polyurethane, polyvinyl chloride, styrene acrylonitrile resin, or copolymers thereof. In one embodiment the suitable material is polyethylene, polypropylene, polyurethane or polycarbonate. In another embodiment, the suitable material is polyethylene, or polypropylene. Other materials, such as silicone or TPE, may also be used.

The apparatus should be generally formed such that apparatus 10 does not substantially deform during the use of apparatus 10. Specifically, when a patient bites on mouthpiece 31, the mouthpiece should not constrict the inner cross-section of center section 20. Further, for embodiments in which the mouthpiece 31 is a separate unit to be connected to an inhaler or spacer, for example, inlet port 13 should also be formed to readily accept an exhaust outlet from the inhaler or a spacer.

Apparatus 10 may be formed by any means in the art used to form mouthpieces of medical devices. In one embodiment the mouthpiece is formed by reaction injection molding.

Figure 2:
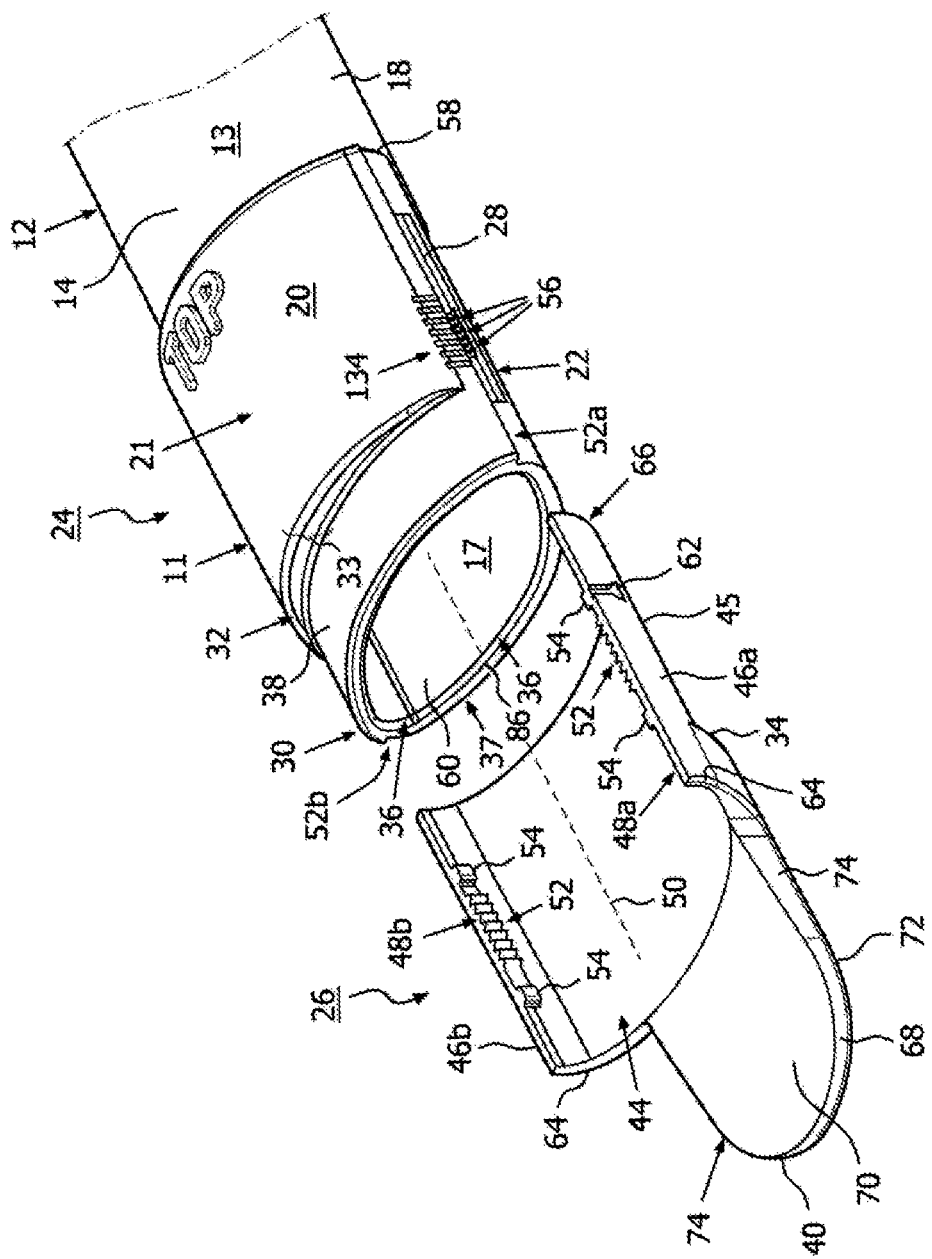
FIG. 2 is an exploded view of the apparatus of FIG. 1.

In the illustrated embodiment, as shown in greater detail in FIG. 2, apparatus 10 is assembled from a plurality of structural elements. The individual elements may be formed by molding or otherwise formed independently from one another. More specifically, mouthpiece 31 as illustrated can be manufactured in two parts, a main mouthpiece body 24 and an adjustable member 26. Adjustable member 26 is configured to slide relative to the main body 24 in a parallel or longitudinal direction with respect to axis 50, as indicated by arrow A in FIG. 1, for example. As will become further evident in the description with respect to FIGS. 3-6, a positioning of adjustable member 26 relative to main mouthpiece body 24 sets a relative offset between an upper and a lower jaw of a user or patient.

Main mouthpiece body 24 may include the above-noted hollow body 11, front end 12, center section 20, and back end 30 formed integrally together. Inlet port 13 functions as a receiving inlet for inhaled pharmaceutical aerosols or medical gases through an inlet aperture 16. Inlet aperture 16 have a shape and configuration adapted to enable the mouthpiece 31 to be removably connected to the exhaust or outlet of a nebulizer, inhaler, or other aerosol generating device. In another embodiment, the inlet 16 is an integral part of the aerosol generating device. In one embodiment, inlet port 13 is defined by a cylindrical projecting wall 14 defining an interior volume. The interior of the inlet port is fluidly connected to the interior of center section 20 of the body 11.

The projecting wall surrounding the interior volume may comprise a plurality of shapes, including, but not limited to, a shape of a right circular cylinder, a frustoconical shape with the wall slightly angled inward, a frustoconical shape with the wall slightly angled outward, or a general right cylinder shape (such as an elliptic cylinder). In one embodiment the inlet port 13 may have any shape which allows for an easier mating with an outlet port of an inhaler device.

Projecting wall 14 terminates on front end 12 with a peripheral edge 15 (shown in phantom). In an embodiment, peripheral edge 15 is generally smooth with slightly rounded corners to aid in mating of an outlet port of an inhaler to the inlet port. In an alternative embodiment, the peripheral edge may have sharp corners. As noted above, in yet another embodiment, peripheral edge 15 may be integrated with an apparatus or device. For example, the edge 15 may be integrally molded as part of an aerosol generating device and not separately defined.

Figure 7:
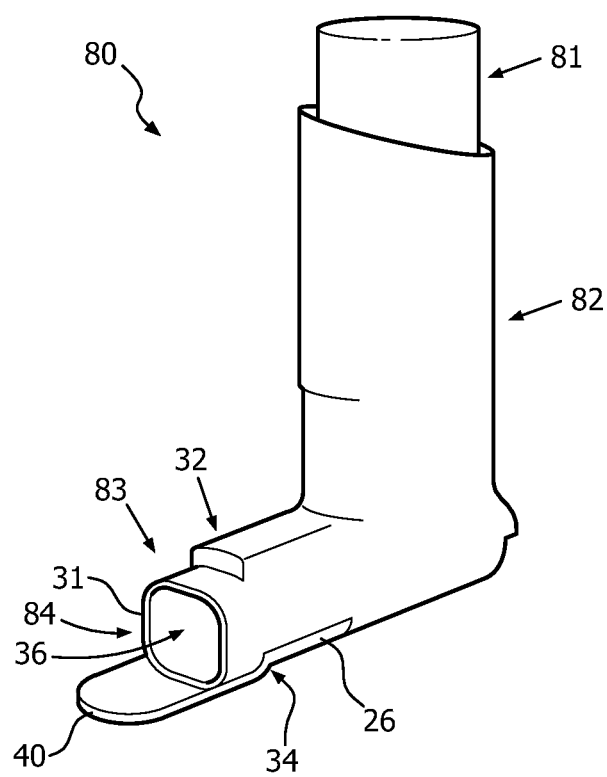
FIG. 7 shows a perspective view of an embodiment of the present disclosure comprising a metered dose inhaler with a stepped mouthpiece.

During the use of the apparatus, the mouthpiece 31 delivers aerosol from an inhaled pharmaceutical aerosol delivery device (not shown in FIGS. 1-6). An inhaled pharmaceutical aerosol delivery device is a device which either generates stored inhaled pharmaceutical aerosol upon actuation to deliver inhaled pharmaceutical aerosol out of an outlet port, or alternatively, is a device through which inhaled pharmaceutical aerosol flows through to an outlet port. Examples of inhaled pharmaceutical aerosol delivery device includes an inhaler (commonly referred to as a puffer), and a spacer. Examples of an inhaler include metered dose inhalers (MDI), dry powder inhalers (DPI), softmist inhalers, or a nebulizer. Examples of nebulizers include pneumatic nebulizers, ultrasonic nebulizers, and mesh nebulizers. FIGS. 7-8B illustrate examples of such devices having mouthpiece 31. These devices typically include a pharmaceutical containing reservoir, and some may contain an actuator. As used herein, the term "reservoir" refers to a pressurized canister, a non-pressurized DPI container for powder, and/or other pressurized or non-pressurized storage devices for containing a pharmaceutical or drug therein. An inhaled pharmaceutical aerosol delivery device also includes devices that deliver condensation aerosols and electro: hydrodynamic aerosols.

Apparatus 10 is designed to be used in concert with a metered dose inhaler in an embodiment. Common metered dose inhalers include, but are not limited to, those sold under the tradenames Airomir™, Ventolin®, Atrovent®, Becloforte®, Benclovent®, Berotec®, Combivent®, Flovent®, Tilade®, Serevent®, Intal®, Vanceril®, and QVAR®.

Mouthpiece 31 as herein disclosed can be used with any device that delivers inhaled pharmaceutical aerosol. The phrase "inhaled pharmaceutical aerosol" refers to any type of medicament that is formulated to be delivered to a patient in aerosolized form into the patient's lungs. For example, for purposes of this disclosure, powder particles of DP's can be considered an aerosol (i.e., aerosol is not limited to liquid particles). As used herein, the term "aerosol" refers to a suspension of solid, solution or liquid particles in a gas. The term "aerosol" also refers to a suspension of a mixture of solid and liquid particles in a gas. The term "aerosol" also refers to liquid particles in a gas, wherein the liquid is a mixture of at least two liquids. Such a mixture can be a homogenous liquid (such as a solution), or it can be a heterogeneous liquid (such as a suspension).

Also, apparatus 10 is designed to work with any aerosol of any common particle size. In an embodiment, the mean aerosol particle size is 0.1 to 10 micrometers. In another embodiment, the mean aerosol particle size is 0.5 to 5 micrometers. In yet another embodiment, the aerosol particle size is submicron size. An example of particles with submicron size is nanoparticles.

For a separately formed mouthpiece 31, the mating of inlet port 13 with an outlet port of an inhaled pharmaceutical aerosol delivery device can be achieved in several ways. In one embodiment, an outlet port of the inhaled pharmaceutical aerosol delivery device is friction fitted through inlet aperture 16 into inlet port 13 of apparatus 10. In this embodiment an outer surface of the outlet port is in contact with an inner surface 17 of the tubular body. In another embodiment, mouthpiece 31 may be configured to be attached to a spacer or valved holding chamber that is attached to an inhaled pharmaceutical aerosol delivery device. For example, spacers and chambers may be used with MDIs. Thus, it is to be understood that apparatus 10 may be directly or indirectly attached in a number of ways to a delivery device.

In the embodiment illustrated in the FIGS., inner surface 17 is smooth. Such smoothness aids in the mechanism of friction fitting. In an alternative embodiment, inner surface 17 has geometric features which help to retain the outlet port of the inhaled pharmaceutical aerosol delivery device so it is matched to the corresponding features on the outlet port of the inhaled pharmaceutical aerosol delivery device. Such geometric features include ridges and other protruding features, and valleys and other intruding features. Such geometric features on the inner surface 17 in such embodiment are coordinated to the matching features on the outer surface of the outer port of inhaled pharmaceutical aerosol delivery device.

In an alternative embodiment, the outlet port of the inhaled pharmaceutical aerosol delivery device fits over inlet port 13; namely, outer surface 18 of projecting wall 14 is in contact with the inner surface of the wall of the outlet port of the inhaled pharmaceutical aerosol delivery device. In an alternative embodiment, outer surface 18 has geometric features which help to retain the outlet port of the inhaled pharmaceutical aerosol delivery device by matching to the corresponding feature on the outlet port of the inhaled pharmaceutical aerosol delivery device. Such geometric features include ridges and other protruding features, and valleys and other intruding features. Such geometric features on the outer surface 18 in such embodiment are coordinated to the matching features on the inner surface of the outer port of inhaled pharmaceutical aerosol delivery device.

Center section 20 of the tubular body 11 is attached on one end to inlet port 13 and on the other end with a mouthpiece 31. Center section 20 is hollow and is in fluid communication with inlet port 13. The cross-section of the center section can be of any two dimensional shape, so long as that it of sufficient size for a mouthpiece to fit into a patient's mouth to deliver the inhaled pharmaceutical aerosol. In the embodiment shown in the FIGS., center section 20 has an elliptic cross-section. In this embodiment, the minor axis of the ellipse that defines the cross-section of the center section is in the vertical direction, and the major axis of the ellipse that defines the cross-section of the center section is in the horizontal direction. In other embodiments, the cross-section of center section 20 may be circular, ellipsoidal, oval, square, square with rounded corners, square with four curvilinear edges, rectangular, rectangular with rounded edges, rectangular with two curvilinear edges, or rectangular with four curvilinear edges, among others. The area of the cross section of bore 60 at narrowest point of bore 60 is defined as the cross section. Such cross section is measured in $mm^2$. The size of cross section area in the apparatus of the present disclosure may be between 50 and 500 $mm^2$, and in one embodiment between 100 and 300 $mm^2$.

As illustrated in FIG. 2, center section 20 of tubular body 11 has a top side 21 and a bottom side 22. Both top side 21 and bottom side 22 stretch from a border between center section 20 and inlet port 13 to the front portions of the mouthpiece 31.

In order to use apparatus 10 properly, apparatus 10 needs to be positioned between the upper and lower teeth of the patient properly. In one embodiment, the patient places top side 21 of apparatus 10 in contact with his/her top teeth and bottom side 39 of the apparatus 10 with his/her bottom teeth. In one embodiment, the bottom side 39 of the apparatus that engages the patient's lower teeth is provided on an adjustable member 26 that is movable relative to the tubular body 11. In an embodiment, top side 21 is marked as shown in FIGS. 1 and 2 to indicate to the user of the apparatus the axial orientation of apparatus 10. Such markings may be in form of writing, symbols, or juvenile drawings, although any suitable indicia may be used.

Center section 20 terminates at back end 30 of mouthpiece 31. Mouthpiece 31 comprises outlet aperture 36, through which inhaled pharmaceutical aerosol is introduced into the oral cavity of a patient.

In the embodiments illustrated, mouthpiece 31 comprises a first (or upper) step 32. Although in the illustrated embodiments the steps 32 and 34 are shown as what looks like a step that might be associated with a flight of stairs, for purposes of this disclosure, the term "step" is defined as a surface for receiving at least a portion of teeth or a tooth. Thus, throughout this disclosure, it is to be understood that "step" may comprise a raised surface, a surface with a difference in thickness, an opening, groove, crevice, or gap, or the like that is positioned or configured to engage teeth of the user. As shown in FIGS. 1-6, first (or upper) step 32 is a raised surface which forms a step on top side 21 of center section 20. The step 32 includes a first riser 33 and an edge 41. In the illustrated embodiment, the step 32 has a riser portion 33 that faces towards the back end 30.

Mouthpiece 31 further comprises an area 38 where a patient's upper teeth are placed. The upper front teeth are placed so that the upper front teeth of the patient are contacted with top side 21 and the apparatus is manipulated so that the front of the upper front teeth are pushed against first (or upper) riser 33. In one embodiment, the incisal surfaces of the maxillary central incisors engages (or contacts) with area 38, while at the same time the facial surfaces (also referred to as the buccal surfaces) of the maxillary central incisors engage with riser 33. In an alternative embodiment at least one of the incisal surfaces of at least one of the maxillary lateral incisor also engages with area 38. In another alternative embodiment at least one of the facial surfaces of at least one the maxillary lateral incisors also engage with riser 33. In yet another embodiment the incisal surface of at least one of the maxillary lateral incisors engages with area 38, while at the same time the facial surface of at least one the maxillary lateral incisors also engages with riser 33.

Provided adjacent the bottom of the tubular body 11 of mouthpiece 31 is adjustable member 26. As previously noted, adjustable member 26 may be configured to move or slide relative to the main body 24 in a parallel or longitudinal direction with respect to axis 50 (see arrow A in FIG. 1). Adjustable member 26 may comprise an attachment portion 44 that attaches to main body 11. Attachment portion 44 of adjustable member 26, in one embodiment, at least partially surrounds or encompasses body 11. Attachment portion 44 may, in one embodiment, comprise a shape corresponding to at least the bottom portion 22 of center portion 20. In an embodiment, attachment portion 44 is comprised of a portion of an elliptical shape corresponding to an outer surface of the body 11. Attachment portion 44 may have sides 46a and 46b which are on opposite sides of the body 11. In an alternate embodiment, adjustable member 26 may comprise a sleeve which substantially surrounds the body 11 of main body 24.

In an embodiment, attachment portion 44 is connected to body 11. Attachment portion 44 may be snap fit to bottom side 22 of apparatus 10, for example. In the illustrated embodiment, body 11 comprises a groove or channel 28 on one or both of its sides for receiving a part of attachment portion 44. As shown in FIG. 2, for example, the inside surfaces of sides 46a and 46b may comprise at least connection portion 54 (e.g., in the form of a projection) for connecting attachment portion 44 to body 11. The connection portion(s) 54 may be sized to be inserted into the channel 28 of the body, for example. In another embodiment, one or more projections may be formed on the body 11 and the groove formed in the adjustable member 26. It should be appreciated that any suitable slidable connection between body 11 and adjustable member 26 can be used. Also, the attachment portion 44 can also be assembled to have a removable connection, such that adjustable member 26 may be removed for cleaning, for example. For example, attachment portion 44 may be sufficiently flexible to enable a slight bending therein to remove the connection portion 54 from channel 28.

In an embodiment, the positioning of adjustable member 26 relative to the main mouthpiece body 11 is designed to set a relative offset therebetween, thereby offsetting an upper and a lower jaw of a user or patient when apparatus 10 is in use. Thus, adjustable member 26 is provided with a step structured to impart a selected amount of mandibular advancement or retraction. In the illustrated embodiment, adjustable member 26 comprises a second (or lower) step 34. Second (or lower) step 34 is a surface which forms a step on bottom side 45 of attachment portion 44. In the illustrated embodiment, the step 34 faces forward (towards front end 12), meaning that looking along bottom side 22 of apparatus from front end 12 towards back end 30, a second (or lower) riser 35 of second (or lower) step 34 is visible. Second riser 35 also includes edge 42 of second step 34 (shown in FIGS. 3 and 5).

Adjustable member 26 further comprises an area 39 where a patient's lower teeth are placed. The lower front teeth of the patient are placed so that the lower front teeth are in contact with the bottom side 45, and the apparatus is manipulated so that the back of the lower front teeth are pushed against second (or lower) riser 35. In one embodiment of the disclosure, the incisal surfaces of at least one of the mandibular central incisors or mandibular lateral incisors engage with area 39, while at the same time at least one of the lingual surfaces of the mandibular central incisors or mandibular lateral incisors engage with riser 35. Any combination of simultaneous engagements or contacting of incisal surfaces of mandibular incisors with area 39 and engagements or contacting of lingual surfaces of mandibular incisors with riser 35 are satisfactory.

The terms "contact" and "engage" of a tooth surface with a surface of the apparatus 10 does not necessarily mean a full or a complete matching of the tooth surface with a portion of the surface of the apparatus. It is sufficient if only a small portion, such as a single point, of the tooth surface contacts a small portion of the surface of the apparatus 10. Thus, in one embodiment the facial surface of a maxillary incisor can engage/contact first (or upper) riser 33 only on edge 41 of first (or upper) step 32. In another embodiment, the lingual surface of a mandibular incisor can engage/contact second (or lower) riser 35 on edge 42 of second (or lower) step 34.

Also, it is to be understood that the location of the first (or upper) and second (or lower) steps 32, 34 should not be limiting and can be switches from the illustrated embodiment. For example, the adjustable member (without a tongue depressor) may be positioned on a top surface of body 11 so that top step 32 is movable relative to the body 11, and the lower step 34 is fixed on the lower side of tubular body 11. In one optional embodiment, the body 11 has a fixed tongue depressor provided thereon.

The relative position or distance of first (or upper) step 32 to second (or lower) step 34 on apparatus 10 can be set in accordance with one embodiment. The step offset, measured in millimeters, is the distance along the axis 50, between the position of the first (or upper) step 32 relative to the second (or lower) step 34. Different values of step offset of the mouthpiece are possible. Step offset value of 0 mm (zero) means that first (or upper) step 32 is longitudinally aligned with second (or lower) step 34. A positive offset value, such as in FIGS. 5 and 6, indicates that first (or upper) step 32 is further back along axis 50 (i.e., closer to back end 30 of mouthpiece 31) than is second (or lower) step 34. In an embodiment, movement of adjustable member 26 is configured to adjust or impart a selected amount of mandibular displacement (e.g., advancement or retraction) to a patient. In an embodiment, movement of adjustable member 26 adjusts a distance between the first (or upper) step 32 and second (or lower) step 34.

The phrase "further back" or "further towards" indicates the position of the steps relative to each other with respect to the axis 50 passing through the center of the apparatus 10. The position of the intersection of an imaginary right angle projection line from the axis 50 of the apparatus 10 to the center of one step is compared to the position of the intersection of an imaginary right angle projection line from the axis 50 of the apparatus 10 to the center of the other step. The step of which the intersection of the projection line is further back along the axis of the apparatus is considered to be further back, or further towards the end (e.g., back end 30 or front end 12) of the apparatus 10.

In an embodiment, at least one projection 52 is provided on the sides 46a and 46b of attachment portion 44. In the illustrated embodiment, a plurality of projections 52 is provided in the form of spaced teeth. Also, the groove or channel 28 may comprise a plurality of cooperative spaced teeth or detents 56 therein. The at least one projection 52 of the adjustable member 26 is received in spaced recesses between the teeth or detents of the channel 28 of body 11. In another embodiment, the at least one projection is provided on the body 11 and received within spaced recesses in the adjustable member 26. Each tooth, projection, or recess may correspond to a predetermined setting for determining an offset. Therefore, when the adjustable member 26 is moved in the longitudinal direction (parallel to axis 50), the at least one projection 52 is configured to be moved into cooperative engagement with one of the spaces between teeth or detents 56.

The predetermined settings may correspond to predetermined intervals indicating offset values for the first (or upper) and second (or lower) steps 32 and 34 with regard to the position of the lower teeth (or lower jaw) with respect to the upper teeth (or upper jaw). For example, when the upper front teeth are placed on area 38 and against first (or upper) riser 33, while at the same time placing the lower front teeth on area 39 and against second (or lower) riser 35, the lower jaw may be pushed unnaturally forward (e.g., see the position of the risers in FIG. 5). Even with a step offset value of 0 mm (zero millimeters), the lower teeth may be advanced forward compared to the upper teeth, as the natural position of teeth in most patients is that the upper front teeth fit slightly over the lower front teeth. Hence, by moving the adjustable member 26, the offset can be adjusted to suit each individual patient. Such movement is inhibited by engagement between the at least one projection (or teeth) and the at least one recess (or spaced teeth) between the body and adjustable member. However, forced manual relative movement between the body and the adjustable member can overcome the inhibiting force as a result of slight flexure of the inter-engaging parts. The amount of force to effect movement between offset positions can be engineered as desired.

As shown in FIG. 1, other markings 134 may be optionally provided on body 11 to indicate relative offset between the steps. For example, an indicator 62 may be included on one or both sides 46a and/or 46b of attachment portion 44 for alignment with an alignment marking 134 that corresponds to an offset value for steps 32 and 34. Numeric indicia 136 may also be provided on the body 11 to indicate the measured offset value for each alignment marking 134. In another embodiment (not shown), the indicator 62 can be provided on the body 11 and the markings 134 and/or indicia can be provided on adjustable member 26. Offsets in the non-limiting range of +2 to −4 may be provided. In an embodiment, markings 134 and/or indicia 136 are oriented on the apparatus in a manner that is readable by or towards the patient, so that the patient can achieve proper orientation of the apparatus when self-administering an aerosol drug. The projection 52 and recesses 56 may be used to set the first (or upper) step 32 and second (or lower) step 34 to an offset of negative or positive value and should not be limited to those illustrated.

Movement of adjustable member 26 may be limited by the amount of projections or recesses 56 provided on the body 11. For example, FIGS. 3 and 4 illustrate a side and top view of a cross section, respectively, of the apparatus 10 with adjustable member 26 in a rearward-most position (i.e., adjustable member 26 is pushed or moved towards back end 30). In this case, the first (or upper) step 32 and second (or lower) step 34 impart a negative offset (e.g., −2) when the risers are engaged with the teeth of a patient in aerosol delivery. FIGS. 5 and 6 illustrate a side and top view of a cross section, respectively, of the apparatus 10 with adjustable member 26 in a forward-most position (i.e., adjustable member 26 is pushed or moved towards front end 12). In this case, the first (or upper) step 32 and second (or lower) step 34 impart a maximum or positive offset (e.g., +4) (mandibular advancement) when the risers are engaged with the teeth of a patient in aerosol delivery.

Also, body 11 may also comprise a limiting edge 58 at a point where inlet port 13 and surface 69 of center section 20 meet (as shown in FIG. 5), in order to prevent the sleeve section 26 from being further pushed along body 11 towards front end 12, or removed therefrom.

Additionally, sides 46a and 46b of attachment portion 44 may have upper edges 48a and 48b, respectively, which are aligned and guided along guide edges 52a and 52b of the apparatus 10. Upper edges 48a and 48b of attachment portion 44 may be provided along the length of the attachment portion 44 and terminate at a front edge 64 of the attachment portion 44. When assembled, the upper edges 48a and 48b are flush with edges 52a and 52b and are guided to move adjacent thereto (along with movement via channel 28).

When in the rearmost position as shown in FIG. 3, for example, front edge 64 of attachment portion 44 may be aligned with a forward edge 37 of outlet aperture 36 of back end 30 so that the surfaces of edge 64 and edge 37 may be substantially flush. When in the forward-most position as shown in FIG. 5, for example, a rear edge of attachment portion 44 may be aligned with limiting edge 58.

Figure 9:
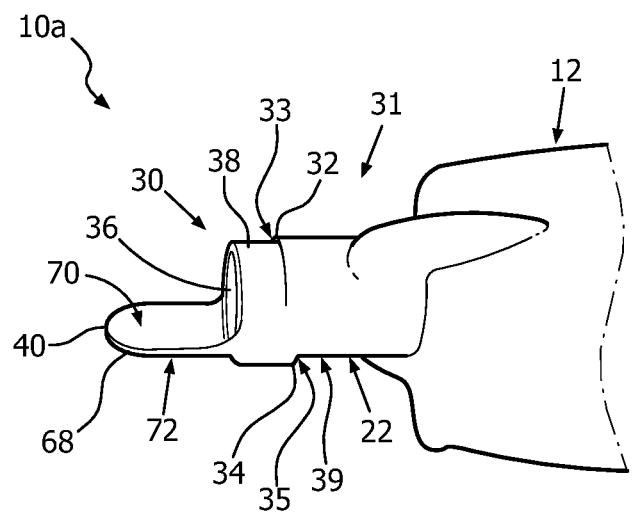
FIG. 9 is a perspective view of an alternate embodiment of an apparatus of the present invention.
Figure 10:
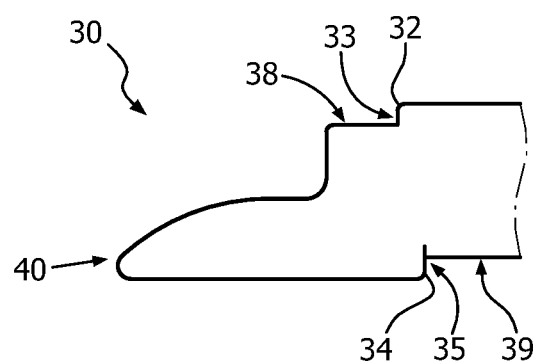
FIG. 10 shows a detailed view of a portion of the apparatus of FIG. 9.

In the illustrated embodiment, apparatus 10 optionally comprises a tongue depressor 40. Tongue depressor 40 may extend from the bottom side of main mouthpiece body 24. In an embodiment, adjustable member 26 comprises tongue depressor 40. For example, in the illustrated embodiment of FIGS. 1-6, the tongue depressor 40 is integrally formed to extend from attachment portion 44. In an alternate embodiment, tongue depressor 40 may be configured to be integrally formed with mouthpiece 31 so as to extend from back end 30, as shown in FIGS. 9 and 10, for example. Tongue depressor 40 is disposed on the mouthpiece such that (i) it does not interfere with the flow of air or aerosol along the inhalation airflow-path and (ii) the apex of a patient's tongue fits underneath the tongue depressor 40 so as to prevent the tongue from occluding a flow of aerosol through the mouthpiece 31 (or apparatus 10).

Specifically, the tongue depressor 40 includes a tongue contact portion 68 extending from the attachment portion 44. Tongue contact portion 68 comprises an upper part 70, lower part 72, and sides 74. In an embodiment, the upper part or surface 70 is curved concavely and the lower part or surface 72 is curved convexly in order to comfortably fit into a patient's mouth. The sides 74 and edges of the tongue contact portion 68 are generally smooth with slightly rounded corners. At least lower part 72 of tongue contact portion 68 contacts a patient's tongue when inserted into the mouth and jaws are clamped onto areas 38 and 39. Tongue contact portion 68 presses the tongue downwardly in order to minimize a natural arch of the tongue and, therefore, any obstruction of the flow of aerosol.

As noted above, in one embodiment, the tongue depressor can be used with an apparatus 10a having a fixed (rather than adjustable) offset as shown in FIGS. 9 and 10. Apparatus 10a may include components similar to those represented in the implementation of FIGS. 1-6, and as described in detail above. Accordingly, FIGS. 9 and 10 includes many of the same reference characters that correspond to the components described above. As shown in the detailed view in FIG. 10, mouthpiece 31 includes upper step 32 on a top side facing back end 30 and lower step 34 on a bottom side facing front end 12. In an optional embodiment, upper step 32 may be provided further towards back end 30 than lower step 34. In this embodiment, both steps 32 and 34 are provided on the body 11 in a fixed predetermined relationship. That is, the distance for offsetting a patient's jaws is predetermined and not adjustable. For example, in one embodiment both steps may be integrally molded as a one piece structure. Tongue depressor 40 extends from bottom side 22 and prevents a tongue from occluding a flow of aerosol through mouthpiece 31 during use. Apparatus 10a may be configured such that it may be used as a retrofit kit to be placed with and/or mounted on existing products or devices, such as any of the inhaled pharmaceutical aerosol delivery devices noted above. Apparatus 10*a* may also be formed from suitable materials, such as those previously noted. In a particular embodiment, apparatus 10*a* is formed from a silicone material. The silicone material may flex slightly, for example when it receives pressure from the patient's teeth. In another embodiment, the material in any of the foregoing embodiments (and any portions thereof) can be made from plastic and then overmolded with a more flexible material such as silicone, rubber, or other elastic material.

A method of use of apparatus 10 is now discussed with regard to the embodiment shown in FIGS. 1-6. During use, the apparatus is positioned between the upper and lower teeth of the patient. The patient takes the apparatus into his/her mouth and introduces the inhaled pharmaceutical aerosol into the inlet port as for the inhaled pharmaceutical aerosol to flow through the device, into the patient's oral cavity, and finally into the patient's lungs. When a patient uses apparatus 10, the patient pushes the upper front teeth against first (or upper) step 32 and pulls the lower teeth against the second (or lower) step 34 of the apparatus 10. The patient's tongue should be positioned below the tongue depressor 40 and in contact with its lower part 72. Generally, this opens up the upper airway to deliver the inhaled pharmaceutical aerosol into patient's lungs. However, the offset provided by the first (or upper) step 32 and second (or lower) step 34 when initially inserted into the patient's mouth may be adjusted to further open (or close) the patient's airway by sliding the attachment portion 44 of the adjustable member 26 with respect to hollow body 11 in a longitudinal direction that is parallel to axis 50. This adjustment may be made with the apparatus within the patient's mouth or outside the patient's mouth.

A patient is a person to whom it is desired that an inhaled pharmaceutical aerosols be delivered; the definition of the term "patient" includes both a sick person as well as a healthy person. Apparatus 10 may be held by patient 60 via clamping down on the body 11 and adjustable portion 26 using the patient's maxillary incisors and mandibular incisors. Incisal surface of maxillary incisor engages with area 38, facial surface of maxillary incisor connects with first (or upper) riser 33, incisal surface of mandibular incisor engages with area 39, and lingual surface engages with edge 42.

The stepped mouthpiece and tongue depressor (whether the steps are movable or fixed) results in combined opening and advancement of the jaw and prevention of the tongue causing occlusion. This not only opens the airway, but also causes an appropriate positioning of the patient's tongue. Additionally, in the adjustable embodiment, the herein described apparatus 10 allows the offset of the teeth and the opening between the teeth to be adjusted to open the airway behind the tongue to suite the individual patient.

It should be understood that the herein described illustrated embodiment of adjustable member 26 should not be limiting. For example, although adjustable member 26 is shown as a lower or bottom piece, as noted previously, it is envisioned to be within the scope of this disclosure that member 26 and body 11 may together comprise a single non-adjustable unitary body with an opening therethrough, with no adjustment. Alternatively, adjustable member 26 may comprise an upper piece that is adjustable. Also, the features described with regard to the adjustability of the steps (32 and 34) and tongue depressor 40 are not dependent on each other and can be used separately.

The adjustable aspect of the apparatus described above may be used by a physician or nurse to find the correct offset setting for an individual patient, and then, using the offset reference number/indicia shown, order a fixed offset mouthpiece to suite the individual patient, such as the type disclosed in U.S. Ser. No. 61/140,138 filed Dec. 23, 2008 and hereby incorporate by reference in its entirety, or apparatus 10*a* as shown in FIG. 9. Additionally, one may determine an offset required to select or order a fixed mouthpiece by using a method for measuring the area of the airway (such as acoustic pharyngometry) with the herein disclosed adjustable mouthpiece to determine the optimum position for jaw offset, opening between the jaws, and size of tongue depressor.

To change the extent of the opening of the jaws, adjustable members 26 can be used which have different thicknesses (or heights) to increase or decrease the opening between the jaws.

The disclosed adjustable member 26 and tongue depressor 40 should not be limited with regard to their use or type of apparatus 10. For example, apparatus 10 may be a separate mouthpiece for use in aerosol delivery, or an entire apparatus to aid aerosol delivery to a patient, including an aerosol generating device for generating a flow of aerosol.

In some embodiments, an apparatus may incorporate main mouthpiece body 24 and adjustable member 26 into the structure of an inhaled pharmaceutical aerosol delivery device. For example, in one embodiment, the inhaled pharmaceutical aerosol delivery device comprising the disclosed adjustable offset and/or tongue depressor is a metered dose inhaler. Generally, a metered dose inhaler comprises at least two components: a canister, and an actuator. The canister can also be referred to as an aerosol generating device. The canister contains a drug which is to be delivered to patient's lungs, a liquefied gas propellant, and other excipients, such as a stabilizer. The canister also comprises a metering dose valve with an actuating stem. The actuator comprises a discharge nozzle which mates with the actuating stem. The patient using the inhaler presses down on the top of the canister, while supporting the lower portion of the actuator. The actuator includes, or is in communication with, the mouthpiece. Actuation of the device releases a single metered dose of liquid propellant that contains the drug. A breakup of the volatile propellant into droplets, followed by rapid evaporation of the droplets yields micron-sized aerosol particles containing the drug.

In the following descriptions, certain parts are labeled with the same reference numerals as in previous embodiments so as to indicate similar parts as can be appreciated by those skilled in the art.

The peripheral edge of the mouthpiece of the present disclosure can have any shape appropriate to define the outlet aperture. In various embodiments, the outlet aperture can have a shape of a circle, an ellipse, an oval, a square, a square with rounded corners, a square with four curvilinear edges, a rectangle, a rectangle with rounded edges, a rectangle with two curvilinear edges, a rectangle with four curvilinear edges, or other suitable shapes.

An embodiment of a metered dose inhaler comprising the disclosed adjustable member 26 and tongue depressor 40 is illustrated in FIG. 7. Metered dose inhaler 80 comprises a reservoir in the form of a canister (or aerosol generating device) 81, and actuator 82. The inhaler comprises mouthpiece 31, which at back end 84, contains outlet aperture 36, defined by peripheral edge 86. The exemplary embodiment in FIG. 7 shows the shape of aperture 36 defined by peripheral edge 86 as a square with four curvilinear edges. The mouthpiece further comprises an first (or upper) step 32 on upper side of mouthpiece 31, and a second (or lower) step 34 on lower side of mouthpiece 31, as described above. More specifically, in the illustrated embodiment, second step 34 is provided on a bottom side of adjustable member 26. Inhaler 80 also has tongue depressor 40 extending from a bottom side of mouthpiece 31.

In another embodiment of the present invention, the adjustable member 26 and tongue depressor 40 are incorporated into the structure of a dry powder inhaler. Any dry powder inhaler in which a patient places a mouthpiece of the dry powder inhaler between the patient's teeth is may be adapted to incorporate the stepped mouthpiece. A dry powder inhaler may be a single-dose device, or a multiple-dose device. Examples of dry powder inhalers include Aerolizer®, Handi-Haler™, Flexhaler®, Diskus®, and Twsthaler®.

Figure 8A:
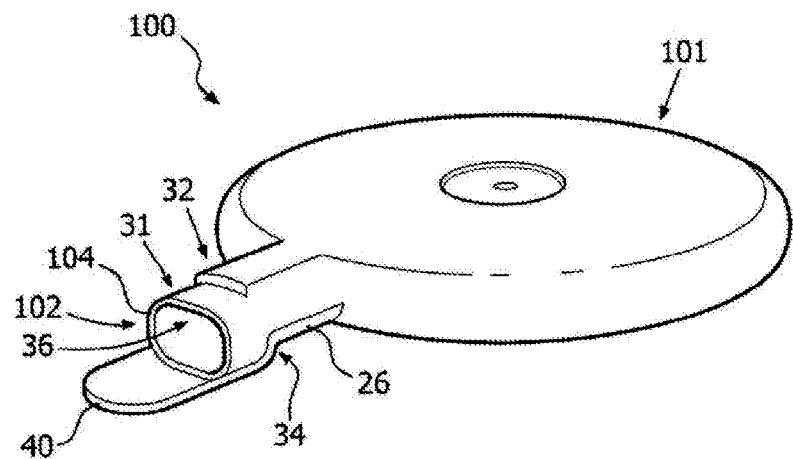
FIG. 8A shows a perspective view of an embodiment of the present disclosure comprising a dry powder inhaler with a stepped mouthpiece.
Figure 8B:
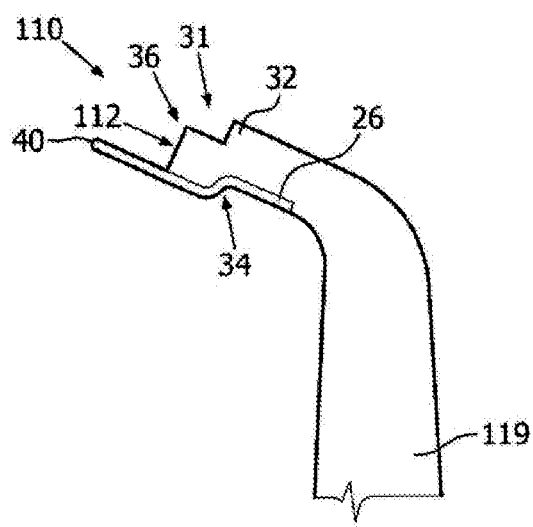
FIG. 8B shows a side elevation view of an embodiment of the present disclosure comprising a portion of a nebulizer with a stepped mouthpiece.

An embodiment of a dry powder inhaler comprising adjustable member 26 and tongue depressor 40 is illustrated in FIG. 8A. Dry powder and/or soft mist inhaler 100 comprises a reservoir 101 and mouthpiece 31. The mouthpiece 31 at back end 102 contains outlet aperture 36, defined by peripheral edge 104. The exemplary embodiment in FIG. 8(a) shows the shape of aperture 36 defined by peripheral edge 104 as a circle. The device further comprises a first (or upper) step 32 on upper side of mouthpiece 31, and a second (or lower) step 34 on lower side of mouthpiece 31, as described above. More specifically, in the illustrated embodiment, second step 34 is provided on a bottom side of adjustable member 26. Dry powder and/or soft mist inhaler 100 also has tongue depressor 40 extending from a bottom side of mouthpiece 31.

In yet another embodiment of the present invention, the adjustable member 26 and tongue depressor 40 are incorporated into the structure of a nebulizer. Any nebulizer in which a patient places a mouthpiece of the nebulizer between the patient's teeth is may be adapted to incorporate the stepped mouthpiece. Examples of nebulizers which may comprise adjustable member 26 and tongue depressor 40 as disclosed herein include pneumatic nebulizers, ultrasonic nebulizers, and mesh nebulizers. Nebulizers of the present disclosure which comprise stepped mouthpieces and adjustable member 26 and tongue depressor 40 also include devices that deliver condensation aerosols and electrohydrodynamic aerosols.

An embodiment of a nebulizer comprising adjustable member 26 and tongue depressor 40 is illustrated partially in FIG. 8B. Nebulizer outlet tube 110 comprises mouthpiece 31, which at back end 112, contains outlet aperture 36. The device further comprises a first (or upper) step 32 on upper side of mouthpiece 31, and a second (or lower) step 34 on lower side of mouthpiece 31. More specifically, in the illustrated embodiment, second step 34 is provided on a bottom side of adjustable member 26. Nebulizer outlet tube 110 also has tongue depressor 40 extending from a bottom side of mouthpiece 31. Nebulizer outlet tube 110 is connected to the rest of the nebulizer (including a pharmaceutical containing reservoir) by tubing 119.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A mouthpiece for an apparatus to aid aerosol delivery to a patient, the mouthpiece comprising:
    a tubular body, the tubular body forming the mouthpiece, the tubular body having a first outer side and a second outer side opposite the first outer side, the tubular body having a medicament outlet end and a distal end opposite the medicament outlet end, the tubular body forming an unobstructed flow path therethrough along a longitudinal axis from the medicament outlet end to the distal end between the first outer side and the second outer side such that with the apparatus installed within a mouth of the patient and aerosol being delivered to the patient, the aerosol freely flows through the tubular body from the distal end through the medicament outlet end that is engaged with the mouth of the patient;
    a first step on the first outer side of the tubular body, the first step being configured to engage one or more top teeth of the patient when the mouthpiece is installed in the mouth of the patient;
    a second step on the outer side of the tubular body opposite the first outer side of the mouthpiece, the second step being configured to engage one or more bottom teeth of the patient when the mouthpiece is installed in the mouth of the patient, wherein the relative positions of the first step and the second step along the longitudinal axis of the mouthpiece are positioned to engage the top teeth and bottom teeth, respectively, of the patient when the mouthpiece is installed in the mouth of the patient, and by such engagement to advance a lower mandible of the patient toward the distal end along the longitudinal axis; and
    a tongue depressor extending from the second outer side and configured to prevent a tongue from occluding a flow of aerosol through the mouthpiece.

2. A mouthpiece according to claim 1, wherein the mouthpiece includes the tubular body and a movable member, wherein the tubular body has thereon either the first step or the second step, and the movable member has the other of the first step or the second step so that a distance between the first step and the second step is adjustable.

3. A mouthpiece according to claim 1, wherein the tubular body comprises an inlet port adapted to attach to an inhaled pharmaceutical aerosol delivery device.

4. A mouthpiece according to claim 3, wherein the inlet port is adapted to attach to an inhaler.

5. A mouthpiece according to claim 2, wherein the first step is formed on the tubular body and the second step is formed on the movable member.

6. A mouthpiece according to claim 2, wherein the tongue depressor is formed on the movable member.

7. A mouthpiece for an apparatus to aid aerosol delivery to a patient, the mouthpiece comprising:
    a tubular body, the tubular body forming the mouthpiece, the tubular body having a first outer side and a second outer side opposite the first outer side, the tubular body having a medicament outlet end and a distal end opposite the medicament outlet end, the tubular body forming an unobstructed flow path therethrough along a longitudinal axis from the medicament outlet end to the distal end between the first outer side and the second outer side such that with the apparatus installed within a mouth of the patient and aerosol being delivered to the patient, the aerosol freely flows through the tubular body from the distal end through the medicament outlet end that is engaged with the mouth of the patient;
    an adjustable member configured to move along the longitudinal axis of the tubular body;
    a first step on the first outer side of the tubular body, the first step being configured to engage one or more top teeth of the patient when the mouthpiece is installed in the mouth of the patient; and
    a second step on the second outer side of the tubular body, opposite the outer side of the mouthpiece, the second step being configured to engage one or more bottom teeth of the patient when the mouthpiece is installed in the mouth of the patient, wherein the first step is formed on one of the tubular body or adjustable member and the second step is formed on the other of the tubular body or adjustable member, and wherein movement of the adjustable member adjusts a longitudinal distance along the longitudinal axis between the first step and the second step such that the relative positions of the first step and the second step along the longitudinal axis of the mouthpiece are positioned to engage the top teeth and bottom teeth respectively and by such engagement to advance a lower mandible of the patient toward the distal end relative to the first step along the longitudinal axis.

8. A mouthpiece according to claim 7, wherein the adjustable member at least partially surrounds the second outer side of the mouthpiece.

9. A mouthpiece according to claim 7, wherein the first step is formed on the tubular body and the second step is formed on the adjustable member.

10. A mouthpiece according to claim 7, wherein a plurality of stop surfaces are positioned between the adjustable member and the tubular body such that the adjustable member moves with respect to the tubular body at predetermined intervals.

11. A mouthpiece according to claim 10, wherein the predetermined intervals are defined by indicia or markings on the tubular body and the adjustable member.

12. A mouthpiece according to claim 10, wherein one or more of the plurality of stop surfaces comprise at least one projection and at least one groove, wherein the at least one projection is formed on one of the tubular body or the adjustable member and the at least one groove is formed on the other of the tubular body or the adjustable member.

13. A mouthpiece according to claim 7, further comprising a tongue depressor configured to prevent a tongue from occluding a flow of aerosol through the mouthpiece.

14. A mouthpiece according to claim 13, wherein the tongue depressor is integral with the adjustable member.

15. A mouthpiece according to claim 7, wherein the tubular body comprises an inlet port adapted to attach to an inhaled pharmaceutical aerosol delivery device.

16. A mouthpiece according to claim 15, wherein the inlet port is adapted to attach to an inhaler.

17. A mouthpiece for an apparatus to aid aerosol delivery to a patient, the mouthpiece comprising:
  a tubular body, the tubular body forming the mouthpiece, the tubular body having a first outer side and a second outer side opposite the first outer side, the tubular body having a medicament outlet end and a distal end opposite the medicament outlet end, the tubular body forming an unobstructed flow path therethrough along a longitudinal axis from the medicament outlet end to the distal end between the first outer side and the second outer side such that with the apparatus installed within a mouth of the patient and aerosol being delivered to the patient, the aerosol freely flows through the tubular body from the distal end through the medicament outlet end that is engaged with the mouth of the patient;
- a first step on the first outer side of the tubular body, the first step being configured to engage one or more top teeth of the patient when the mouthpiece is installed in the mouth of the patient;
- a second step on the second outer side of the tubular body opposite the first outer side of the mouthpiece, the second step being configured to engage one or more bottom teeth of the patient when the mouthpiece is installed in the mouth of the patient;
- an adjustable member configured to move in a longitudinal direction along the longitudinal axis of the tubular body, the first step being formed on one of the tubular body or adjustable member and the second step formed on the other of the tubular body or adjustable member, wherein the relative positions of the first step and the second step along the longitudinal axis of the mouthpiece are positioned to engage the top teeth and bottom teeth respectively and by such engagement to advance a lower mandible of the patient toward the distal end relative to the first step along the longitudinal axis; and
- a tongue depressor extending from the second outer side and configured to prevent a tongue from occluding a flow of aerosol through the mouthpiece.

18. A mouthpiece according to claim 17, wherein the tongue depressor is integral with the adjustable member.

19. A mouthpiece according to claim 17, wherein the adjustable member at least partially surrounds the second outer side of the mouthpiece.

20. A mouthpiece according to claim 17, wherein the first step is formed on the tubular body and the second step is formed on the adjustable member.

21. A mouthpiece according to claim 17, wherein a plurality of stop surfaces are positioned between the adjustable member and the tubular body such that the adjustable member moves with respect to the tubular body at predetermined intervals.

22. A mouthpiece according to claim 21, wherein the predetermined intervals are defined by indicia or markings on the tubular body and the adjustable member.

23. A mouthpiece according to claim 17, further comprising one or more stop surfaces that comprise at least one projection and at least one groove, wherein the at least one projection is formed on one of the tubular body or the adjustable member and the at least one groove is formed on the other of the tubular body or the adjustable member.

24. A mouthpiece according to claim 18, wherein the tubular body comprises an inlet port adapted to attach to an inhaled pharmaceutical aerosol delivery device.

25. A mouthpiece according to claim 24, wherein the inlet port is adapted to attach to an inhaler.

26. An apparatus to deliver pharmaceutical aerosol to a patient comprising:

- a pharmaceutical containing reservoir;
- a mouthpiece operatively connected with the reservoir, the mouthpiece comprising a tubular body, the tubular body having a first outer side and a second outer side opposite the first outer side, the tubular body having a medicament outlet end and a distal end opposite the medicament outlet end, the tubular body forming an unobstructed flow path therethrough along a longitudinal axis from the medicament outlet end to the distal end between the first outer side and the second outer side such that with the apparatus held within a mouth of the patient and aerosol being delivered to the patient, the aerosol freely flows through the tubular body from the distal end through the medicament outlet end that is engaged with the mouth of the patient;
- an adjustable member configured to move in a longitudinal direction along the longitudinal axis of the tubular body;
- a first step on the first outer side of the tubular body; and
- a second step on the second outer side of the tubular body, the first step formed on one of the tubular body or the adjustable member and the second step formed on the other of the tubular body or the adjustable member, such that the relative positions of the first step and the second step are adjustable along the longitudinal axis of the mouthpiece and the relative positions of the first step and the second step are positioned to engage the top teeth and bottom teeth respectively, of the patient when the mouthpiece is installed in the mouth of the patient and by such engagement to advance a lower mandible of the patient toward the distal end relative to the first step along the longitudinal axis.

27. An apparatus according to claim 26, further comprising a tongue depressor extending from the second outer side of the tubular body and configured to prevent a tongue from occluding a flow of aerosol through the mouthpiece.

28. An apparatus according to claim 27, wherein the tongue depressor is integral with the adjustable member.

29. An apparatus according to claim 26, wherein the adjustable member at least partially surrounds the second outer side of the tubular body.

30. An apparatus according to claim 26, wherein the first step is formed on the tubular body and the second step is formed on the adjustable member.

31. An apparatus according to claim 26, wherein a plurality of stop surfaces are positioned between the adjustable member and the tubular body such that the adjustable member moves with respect to the tubular body at predetermined intervals.

32. An apparatus according to claim 31, wherein the predetermined intervals are defined by indicia or markings on the tubular body and the adjustable member.

33. An apparatus according to claim 31, wherein one or more of the stop surfaces comprise at least one projection and at least one groove, wherein the at least one projection is formed on one of the tubular body or the adjustable member and the at least one groove is formed on the other of the tubular body or the adjustable member.

34. An apparatus according to claim 26, further comprising an actuator that causes a flow of aerosol from the pharmaceutical in the reservoir, and wherein the actuator is in communication with the mouthpiece for delivering the flow of aerosol.

35. An apparatus according to claim 26, wherein the apparatus is selected from the group consisting of: a metered dose inhaler (MDI), a dry powder inhaler (DPI), a softmist inhaler, or a nebulizer.

36. A method for selecting a fixed mouthpiece for an apparatus configured to deliver aerosol to a user using an adjustable mouthpiece, the adjustable mouthpiece comprising a body tubular body, the tubular body having a first outer side and a second outer side opposite the first outer side, the tubular body having a medicament outlet end and a distal end opposite the medicament outlet end, the tubular body forming an unobstructed flow path therethrough along a longitudinal axis from the medicament outlet end to the distal end between the first outer side and the second outer side such that with the adjustable mouthpiece installed within a mouth of the patient and aerosol being delivered to the patient, the aerosol freely flows through the tubular body from the distal end through the medicament outlet end that is engaged with the mouth of the patient; a first step on the first outer side of the adjustable mouthpiece; a second step on the second outer side of the adjustable mouthpiece; an adjustable member configured to move in a longitudinal direction along a longitudinal axis of the tubular body from the medicament outlet end to the distal end between the first outer side and the second outer side so as to adjust a longitudinal distance between the first step and the second step to determine an appropriate offset amount between the first step and the second step for the user, and the method comprising:

inserting the adjustable mouthpiece into a mouth of the user, sliding the adjustable member in the longitudinal direction along the tubular body to determine the appropriate offset amount for the user;

selecting the fixed mouthpiece for the apparatus based on the determined offset amount, and advancing a lower mandible of the user, while the fixed mouthpiece is inserted into the mouth of the user, with the fixed mouthpiece having the determined offset amount, wherein the fixed mouthpiece is configured to deliver aerosol to the user, wherein the offset amount imparts a selected amount of mandibular shift to the user.

* * * * *